(12) United States Patent
Slavens et al.

(10) Patent No.: US 10,104,313 B2
(45) Date of Patent: Oct. 16, 2018

(54) METHOD FOR TURBINE COMPONENT QUALIFICATION

(71) Applicant: United Technologies Corporation, Farmington, CT (US)

(72) Inventors: Thomas N. Slavens, Moodus, CT (US); Jeremy Styborski, Manchester, CT (US); Alex J. Schneider, Manchester, CT (US); Lea Kennard Castle, Vernon, CT (US); Rodney H. Warner, Austin, TX (US); James Tilsley Auxier, Bloomfield, CT (US)

(73) Assignee: United Technologies Corporation, Farmington, CT (US)

( * ) Notice: Subject to any disclaimer, the term of this patent is extended or adjusted under 35 U.S.C. 154(b) by 238 days.

(21) Appl. No.: 15/205,874

(22) Filed: Jul. 8, 2016

(65) Prior Publication Data

US 2018/0013959 A1    Jan. 11, 2018

(51) Int. Cl.
*G06K 9/00* (2006.01)
*H04N 5/33* (2006.01)
(Continued)

(52) U.S. Cl.
CPC .................. *H04N 5/33* (2013.01); *G01F 9/00* (2013.01); *G01M 15/14* (2013.01); *G01N 25/72* (2013.01);
(Continued)

(58) Field of Classification Search
None
See application file for complete search history.

(56) References Cited

U.S. PATENT DOCUMENTS 3,566,669 A    3/1971    Lawrence et al.
4,644,162 A    2/1987    Bantel et al.
(Continued)

FOREIGN PATENT DOCUMENTS

EP            2930652 A1    10/2015
WO    WO2010/099109 A1    9/2010

OTHER PUBLICATIONS

Extended European Search Report for EP Application No. 17180368.7, dated Nov. 14, 2017, 7 pages.
(Continued)

*Primary Examiner* — Kevin Ky
(74) *Attorney, Agent, or Firm* — Kinney & Lange, P.A.

(57) ABSTRACT

A method for evaluating a turbine component includes inducing a thermal response of the component at an initial time, capturing a two-dimensional infrared image of the thermal response of the component with a thermal imaging device, wherein the two-dimensional infrared image comprises a plurality of infrared image pixels, generating a two-dimension to three-dimension mapping template to correlate two-dimensional infrared image data with three-dimensional locations on the component, mapping at least a subset of the plurality of infrared image pixels of the two-dimensional infrared image to three-dimensional coordinates using the mapping template, and generating a three-dimensional infrared image and infrared data of the component from the mapped infrared image pixels to three-dimensional coordinates, wherein the three-dimensional infrared image and infrared data is used to qualify the component for use.

16 Claims, 6 Drawing Sheets

(51) Int. Cl.
  *G01F 9/00* (2006.01)
  *G01M 15/14* (2006.01)
  *G06T 7/00* (2017.01)
  *G01N 25/72* (2006.01)

(52) U.S. Cl.
  CPC .......... *G06T 7/0006* (2013.01); *G06T 7/0081* (2013.01); *G06T 2200/08* (2013.01); *G06T 2207/10048* (2013.01); *G06T 2207/30164* (2013.01)

(56) References Cited

U.S. PATENT DOCUMENTS

| | | | |
|---|---|---|---|
| 4,902,139 A | 2/1990 | Adiutori | |
| 4,916,715 A | 4/1990 | Adiutori | |
| 4,978,230 A | 12/1990 | Adiutori et al. | |
| 6,422,743 B1 | 7/2002 | Nirmalan et al. | |
| 6,711,506 B2 | 3/2004 | Bales et al. | |
| 6,732,582 B2 | 5/2004 | Bunker et al. | |
| 6,751,261 B1 | 6/2004 | Olsson et al. | |
| 7,365,330 B1 | 4/2008 | Sun | |
| 7,671,338 B2 | 3/2010 | Key | |
| 7,890,274 B2 | 2/2011 | Bunker et al. | |
| 7,909,507 B2 | 3/2011 | Bunker et al. | |
| 8,477,154 B2 | 7/2013 | Davis et al. | |
| 8,718,989 B2 | 5/2014 | Clifton et al. | |
| 2002/0076097 A1 | 6/2002 | Vaidyanathan | |
| 2007/0217672 A1* | 9/2007 | Shannon | G06T 7/0006 382/152 |
| 2012/0086803 A1* | 4/2012 | Malzbender | G01B 11/026 348/140 |
| 2012/0253201 A1* | 10/2012 | Reinhold | A61B 5/1113 600/473 |
| 2015/0172565 A1* | 6/2015 | Haldeman | H04N 5/33 348/164 |
| 2016/0203602 A1* | 7/2016 | Hayashi | A61B 1/00009 382/128 |
| 2016/0224017 A1* | 8/2016 | Huang | B22F 3/1055 |
| 2016/0292515 A1* | 10/2016 | Jia | B66B 3/02 |
| 2016/0295192 A1* | 10/2016 | Hsu | B66B 1/2408 |
| 2016/0295196 A1* | 10/2016 | Finn | G06T 7/11 |
| 2016/0360185 A1* | 12/2016 | Margalit | H04N 13/271 |

OTHER PUBLICATIONS

J. Dozier et al., "Effect of Viewing Angle on the Infrared Brightness Temperature of Snow", Water Resources Research, vol. 18, No. 5, pp. 1424-1434, Oct. 1982.

* cited by examiner

Fig. 1

$$q = \varepsilon \sigma T^4$$
where
    $\varepsilon$ = emissivity
    $\sigma$ = Stefan Boltzman Constant
    $T$ = temperature
    $q$ = heat flux

METHOD FOR TURBINE COMPONENT QUALIFICATION

BACKGROUND

The present embodiments relate generally to non-destructive inspection methods and, more particularly, to the use of infrared thermography to inspect components of gas turbine engines.

Components of gas turbine engines can be exposed to harsh environments, including high temperatures, which can cause damage to components during operation and reduce a component's effective life cycle. Some turbine components can be cooled during operation to limit damage and limit thermal growth of the component, which can be required for particular applications. Components can be cooled by a cooling fluid applied to a surface of the component or through internal cooling channels. The assessment of a component's cooling efficiency during an inspection process can be used to predict the performance of components within a representative environment during operation. A variety of techniques have been used to assess cooling efficiency, including measuring a cooling fluid flow through a component as well as visual inspection of cooling channels and non-destructive imaging. Thermal inspection of components using infrared thermography has been used to assess cooling effectiveness, however, has generally been limited to point to point spot checks, or pixel by pixel measurements without accounting for three-dimensional spatial variations. Such methods are not capable of providing an accurate measurement of surface temperatures over a three-dimensional surface.

SUMMARY

In one aspect, a method for evaluating a turbine component includes inducing a thermal response of the component at an initial time, capturing a two-dimensional infrared image of the thermal response of the component with a thermal imaging device, wherein the two-dimensional infrared image comprises a plurality of infrared image pixels, generating a two-dimension to three-dimension mapping template to correlate two-dimensional infrared image data with three-dimensional locations on the component, mapping at least a subset of the plurality of infrared image pixels of the two-dimensional infrared image to three-dimensional coordinates using the mapping template, and generating a three-dimensional infrared image and infrared data of the component from the mapped infrared image pixels to three-dimensional coordinates, wherein the three-dimensional infrared image and infrared data is used to qualify the component for use.

In another aspect, a method of evaluating a cooling efficiency of component for use in a gas turbine engine can include uniformly heating the component at an initial time such that surface temperatures are approximately equal at all surface locations on the component, capturing a two-dimensional infrared image of the component at the initial time with a thermal imaging device, wherein the two-dimensional infrared image comprises a plurality of infrared image pixels, generating a two-dimension to three-dimension mapping template to correlate two-dimensional infrared image data with three-dimensional locations on the component, mapping at least a subset of the plurality of infrared image pixels of the two-dimensional infrared image to three-dimensional coordinates using the mapping template, and generating a three-dimensional infrared image and infrared data of the component from the mapped infrared image pixels to three-dimensional coordinates, wherein the three-dimensional infrared image and infrared data is used to qualify the component for use.

The present summary is provided only by way of example, and not limitation. Other aspects of the present disclosure will be appreciated in view of the entirety of the present disclosure, including the entire text, claims and accompanying figures.

While the above-identified figures set forth embodiments of the present invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale, and applications and embodiments of the present invention may include features, steps and/or components not specifically shown in the drawings.

DETAILED DESCRIPTION

Figure 1:
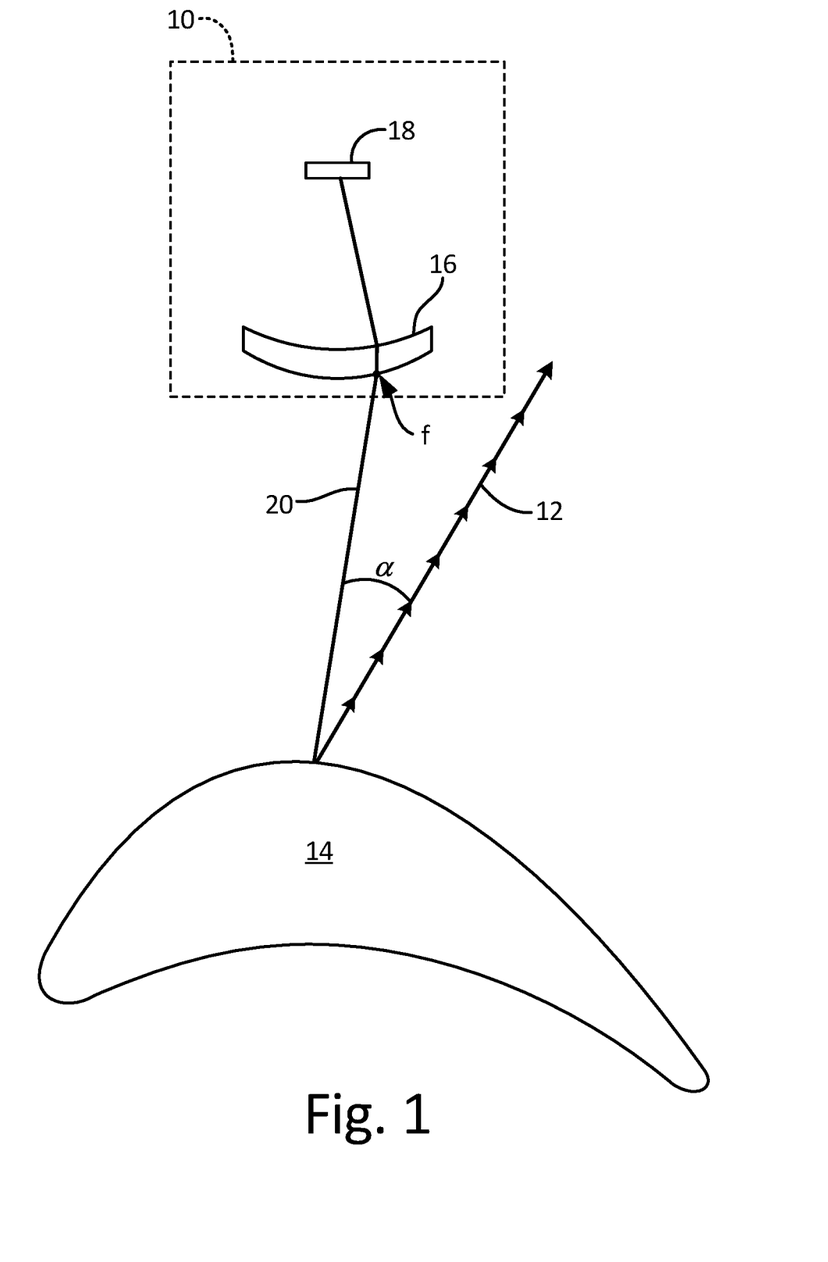
FIG. 1 is a schematic view of an IR acquisition unit being used to detect emitted radiation from a non-planar component.
Figure 2:
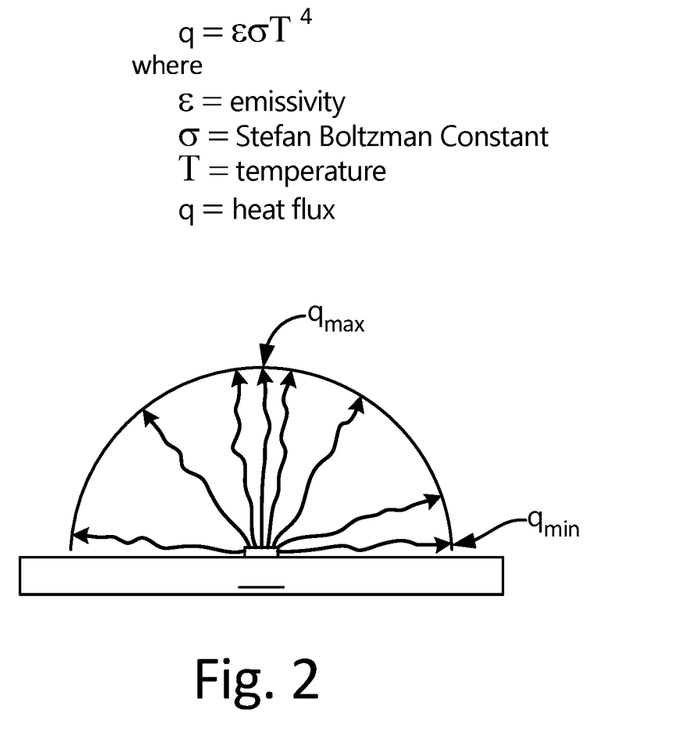
FIG. 2 is a schematic view of the emitted radiation.

Infrared (IR) thermography is a non-contact method to measure temperatures of objects. Instantaneous temperature measurements can be made utilizing temperature-dependent emission of radiation from a surface of an object and a focal plane array to create a two-dimensional thermal (infrared) image of that object. Commercially available IR cameras (otherwise referred to herein as thermal imaging devices or IR acquisition units) are widely used to take static and transient non-contact temperature measurements. FIG. 1 illustrates a schematic view of commercially available IR acquisition unit 10 being used to detect emitted radiation 12 from non-planar or three-dimensional component 14. Commercially available IR acquisition units 10 can utilize optical lenses 16 similar in function to optical digital cameras to direct infrared waves to receptor array 18. While component 14 may have a uniform surface temperature, the resulting two-dimensional infrared image can inaccurately indicate the presence of temperature variations. Such degradation in temperature accuracy of the two-dimensional infrared image occurs due to an angle of the surface relative to a center axis of the camera, surface impurities, and atmospheric moisture. With reference to FIG. 2, in accordance with the Stefan-Boltzman Law of Thermal Radiation, all objects emit radiation at an intensity proportional to the temperature of the object. The ability of IR acquisition unit 10 to accurately measure the temperature of component 14 relies heavily on an effectiveness of the radiation heat transfer between component 14 and IR acquisition unit 10. A maximum magnitude ($q_{max}$) of the radiation heat transfer or heat flux occurs when the surface of component 14 is normal to a focal location (f) of lens 16, as illustrated as line 20 in FIG. 1. However, since objects are three-dimensional, the normality of the surface of component 14 (illustrated as line 12 in FIG. 1) relative to lens 16 is not ensured and a detected heat transfer rate is diminished. The diminished heat transfer rate is typically treated as an adjustment to an emissivity of the surface. As shown in FIG. 1, the heat transfer that occurs from a convex surface of component 14 to camera lens 16 has a surface normal vector 20 that is pointed significantly away from the surface normal (line 12) of component 14, defining perspective or view angle α therebetween. Because most commercial IR acquisition units 10 do not accommodate surface angle obliqueness during image capture, this phenomena must be accounted for later in post-image processing.

Figure 3:
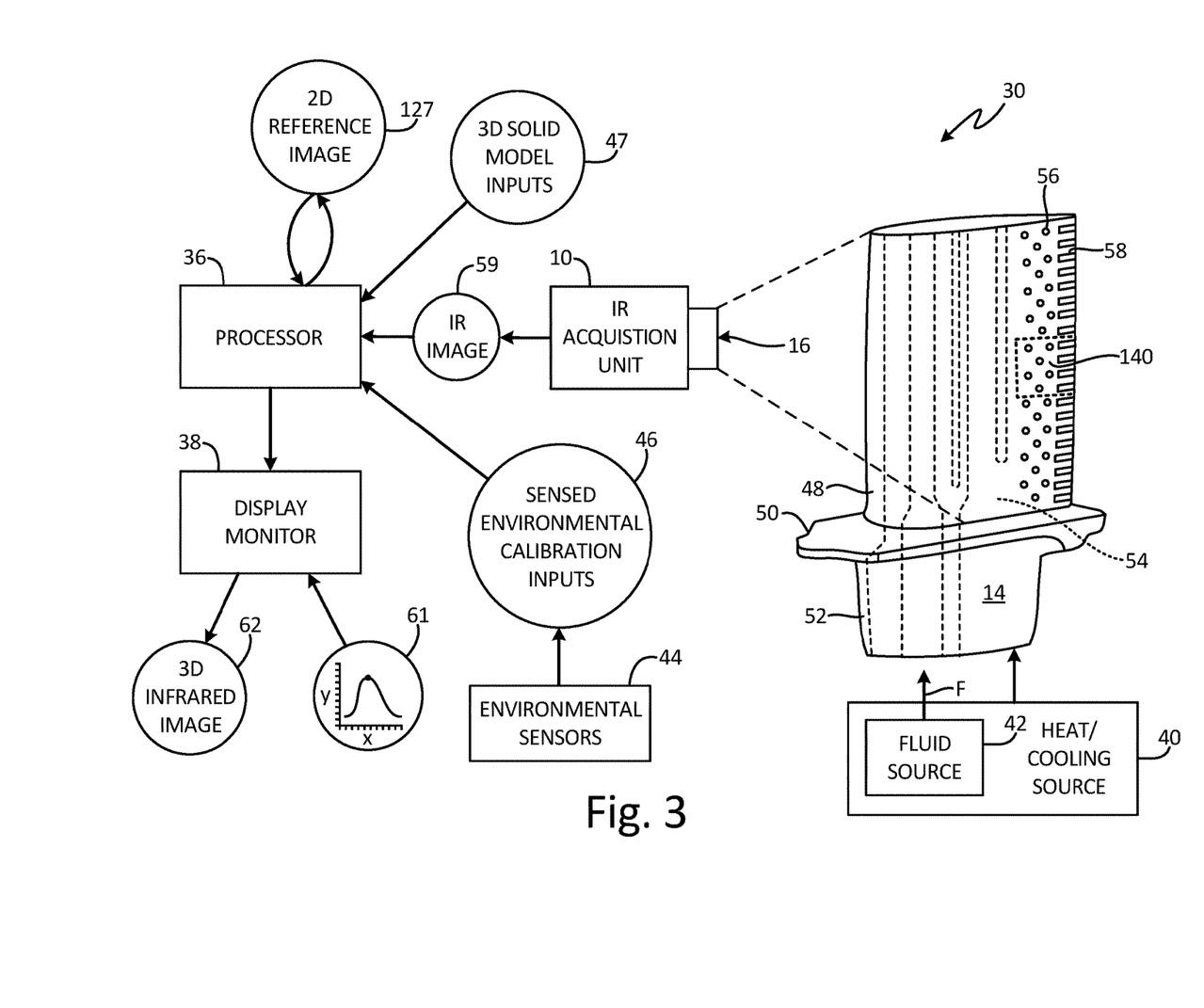
FIG. 3 is a schematic view of an infrared monitoring system.
Figure 4:
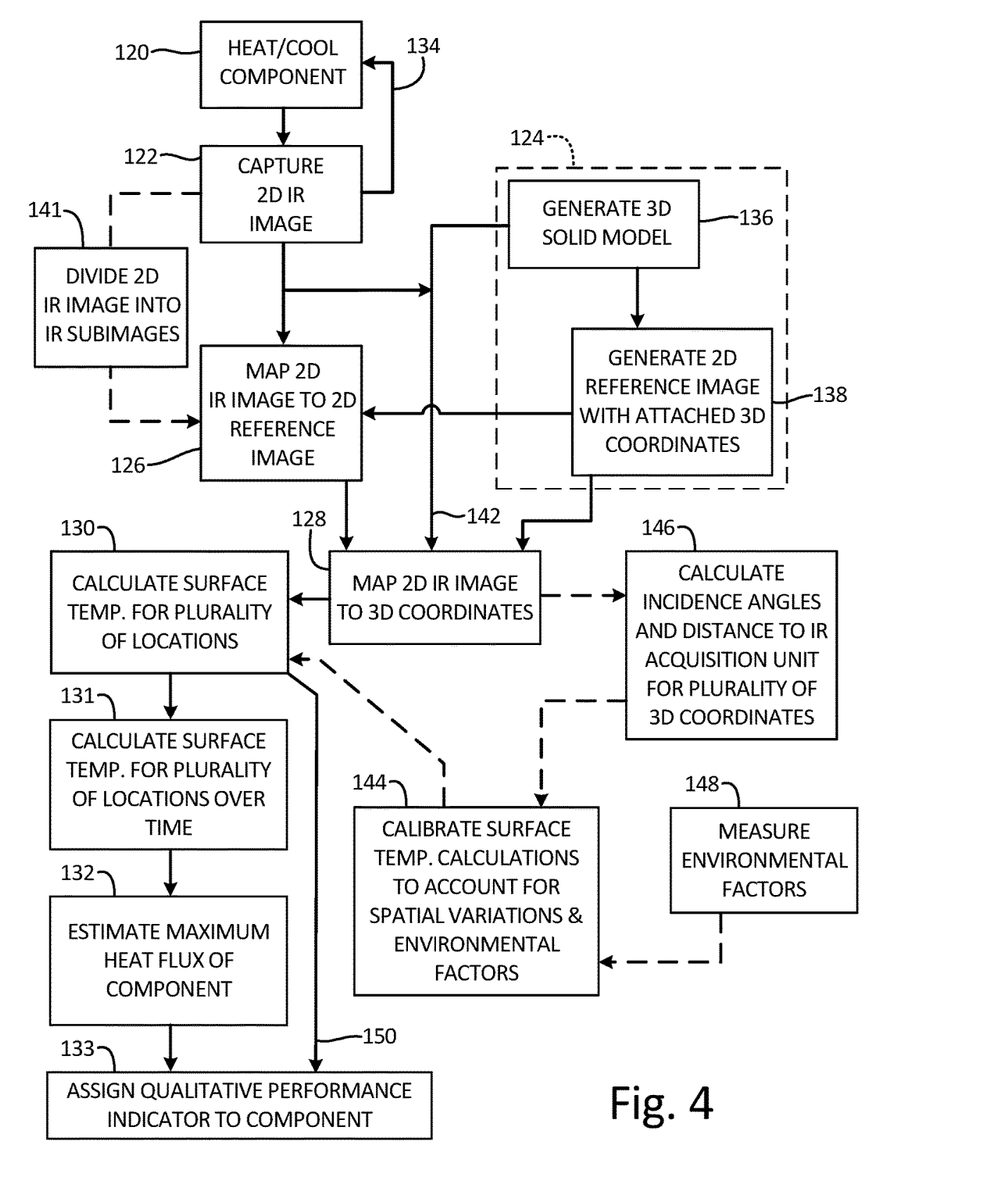
FIG. 4 illustrates a method of evaluating a component based on an infrared response of the component.

FIG. 3 is a schematic view of infrared monitoring system 30. Infrared monitoring system 30 can be used to investigate a thermal response of component 14 to the application or removal of thermal energy. Infrared monitoring system 30 can include IR acquisition unit or infrared camera 10, processor 36, display monitor 38, heat source 40, fluid source 42, environmental sensors 44, calibration inputs 46, and three-dimensional solid model 47. Component 14 can be a turbine blade, having airfoil 48, platform 50, and root 52, as illustrated in FIG. 3, or can be any component, structure, or workpiece of interest. Generally, infrared monitoring system 30 and a method of evaluating component 14 (shown in FIG. 4), can be suited to components 14 that must reach certain thresholds for tolerance to high temperatures or meet a minimum cooling efficiency to be qualified for use. It will be understood by one skilled in the art, that infrared monitoring system 30 and the associated method of FIG. 4 are not limited to investigation of gas turbine engine components, but can be applicable to the assessment of any three-dimensional structure. Component 14 can include one or more internal cooling channels 54 (shown in phantom), which can be used to carry a cooling fluid through component 14 during operation. Cooling channels can extend through component 14 in any manner appropriate for cooling (e.g., serpentine channels and straight-through holes) and can include one or more inlets and outlets of varying shapes and sizes. As shown in FIG. 3, component 14 can have cooling channel outlets in the form of cooling holes 56 and slots 58. In alternative embodiments, component 14 can be a solid structure without internal cooling channels or voids.

IR acquisition unit 10 can be a conventional infrared camera capable of capturing two-dimensional infrared image 59 of component 14 as a stand-alone still image or as part of a video. IR acquisition unit 10 can have lens 16 and optics and electronic controls (not shown). IR acquisition unit 10 can be set forward or aft of component 14 and can be permanently attached to a fixed structure or removably secured to a structure for use in periodic component inspections. IR acquisition unit 10 can capture an object temperature-dependent radiation emission for each pixel of two-dimensional infrared image 59 in an electronic format, which can be sent to processor 36 from IR acquisition unit 10. IR acquisition unit 10 can capture a plurality of two-dimensional infrared images 59 of component 14 and associated thermal radiation emission rates over a period of time to show the thermal response of component 14 to the addition or removal of thermal energy. Generally, infrared images 59 can be still frames captured from an infrared video. The video frame rate and number of pixels can vary as appropriate for varying applications. Generally, a frame rate ranging from 10 to 30 Hz (10-30 images per second) can be used for determining a cooling efficiency of component 14. In the embodiment illustrated in FIG. 3, a 640×480 pixel capture area (roughly 307,000 pixels) is used to evaluate a turbine blade. It will be understood by one skilled in the art that the capture rate and capture area can vary between applications depending on the size of the component and desired resolution.

Corrections for three-dimensional spatial variations along a surface of component 14 and environmental factors, such as environmental humidity, impurities on the surface of component 14, and surrounding radiant bodies, which can affect the radiation emission detected by IR acquisition unit 10, can be included in surface temperature calibrations. Three-dimensional solid model 47 of component 14 can be used for calculating spatial calibrations. Three-dimensional solid model 47 can have the same spatial orientation with respect to camera lens 16 as component 14, such that corrections for camera view angle and a distance to component 14 can be calculated from three-dimensional solid model 47. Environmental calibration inputs can be measured or calculated directly from two-dimensional infrared image 59 or can be measured by external sensors or other known measurement devices. Spatial and environmental calibration inputs can be obtained and entered into a calibration algorithm once during component inspection or can be continuously measured or calculated and input during an inspection process. For example, environmental factors, such as humidity, which can change over a duration of the inspection process, can be continuously measured by environmental sensor 44, and the sensed environmental calibration inputs 46 can be continuously entered into the calibration algorithm. Other environmental factors, including impurities on the surface of component 14 (e.g., a smudge or contamination due to improper cleaning), which can affect an emissivity of component 14, but do not change over time, can be corrected for once at the beginning of the inspection process. Calibration inputs are neither limited to the factors disclosed, nor do calibration inputs have to include each of the factors disclosed. It will be understood by one skilled in the art to include those factors that affect the accuracy of infrared data acquisition.

Processor 36 can acquire inputs from IR acquisition unit 10, sensed environmental calibration inputs 46, and three-dimensional solid model 47, and can compute surface temperatures over a plurality of locations along the three-dimensional surface of component 14. Processor 36 can be any device or machine capable of performing computational tasks or calculations necessary to process information associated with the method disclosed in FIG. 4. In general, processor 36 can compute surface temperatures associated with each of a plurality of infrared images taken over a period of time to calculate how surface temperatures vary over time with the addition or removal of thermal energy to component 14, supplied by heat source 40 or fluid source 42. Display monitor 38 can be coupled to processor 36 to display results 61 computed by processor 36. Results 61 can include, for example, a series of images showing calibrated surface temperatures over the portion of component 14 within viewing range of IR acquisition unit 10 or a calculation of internal heat flux at a plurality of locations. Results 61 can be used to qualify component 14 for use.

FIG. 4 illustrates the method of evaluating component 14 based on infrared response of component 14 to the addition or removal of thermal energy. The method allows the translation of two-dimensional infrared image 59 of component 14, captured by IR acquisition unit 10, to three-dimensional infrared image 62 (FIG. 3) of component 14 and the calculation of surface temperatures over the three-dimensional surface of component 14 and internal heat flux (61, FIG. 3). The method includes (step 120) applying thermal energy to or removing thermal energy from component 14, (step 122) capturing two-dimensional infrared image 59 of component 14, (step 124) generating a two-dimension to three-dimension mapping template that can be used to correlate two-dimensional infrared image data with three-dimensional locations on component 14, (step 126) mapping two-dimensional infrared image 59 to a two-dimensional reference image 127 (FIG. 5A) of component 14, (step 128) mapping two-dimensional infrared image 59 to three-dimensional coordinates using the two-dimension to three-dimension mapping template, (step 130) calculating surface temperatures for a plurality of locations along the surface of component 14, (step 131) calculating surface temperatures for a plurality of locations along the surface of component 14 over a time interval during which the thermal response of component 14 changes, (step 132) estimating a maximum heat flux of component 14 over a period of time from a plurality of infrared images, and (step 133) assigning a qualitative performance indicator, based on calculated surface temperatures or maximum heat flux, to component 14, which can be used to determine end use.

To evaluate component 14 with infrared monitoring system 30, thermal energy can be applied to or removed from component 14 by heat/cooling source 40 (FIG. 3) to produce a thermal response. Heat/cooling source 40 can be any heat or cooling source known in the art, including, but not limited to, an oven, lamp, refrigeration unit, or fluid, such as a flow (F) of gas from fluid source 42 (FIG. 3). In some embodiments, a single infrared image capturing a single thermal response can be used to evaluate component 14. In alternative embodiments, a plurality of infrared images capturing a plurality of thermal responses over a time period during which thermal energy is applied to or removed from component 14, can be used to evaluate component 14. The method utilizing a plurality of infrared images can be used to evaluate cooling efficiency of component 14 via active cooling with cooling fluid flow (F) supplied by fluid source 42. In other applications, infrared images can be captured as component 14 is being heated or being cooled under ambient conditions without the addition of a cooling fluid.

The disclosed method is generally described herein as a method for evaluating cooling efficiency. However, it will be understood by one skilled in the art that the method can be used for any application of infrared thermography to evaluate a three-dimensional component, structure, or workpiece. To evaluate cooling efficiency via active cooling with a cooling fluid, component 14 can first be uniformly heated to a desired temperature, such that surface temperatures are approximately equal at all surface locations of the component, and then cooled with cooling flow (F) through one or more internal channels of component 14 (step 120). The temperature to which component 14 is heated and the temperature of cooling fluid can vary according to the application. Generally, component 14 can be heated to a temperature representative of operational conditions and cooled with a cooling fluid at a temperature representative of operational cooling fluid. Applying thermal energy to and removing thermal energy from component 14 through heating and cooling, can induce a transient thermal response, which can be captured by IR acquisition unit 10. To evaluate cooling efficiency, a plurality of infrared images can be captured over a period of time of component cooling (indicated by arrow 134). Generally, IR acquisition unit 10 can capture an infrared video, from which still infrared images 59 can be obtained. Before actively cooling component 14, IR acquisition unit 10 can be used to capture a first two-dimensional infrared image 59 (step 122). As component 14 is cooled, additional infrared images can be captured. Generally, capture rate can be around 30 Hz (30 images per second), but can vary according to the application. Two-dimensional infrared images 59 captured can each include a plurality of pixels. Each pixel can contain the rate of radiation heat transfer from component 14 to the IR acquisition unit 10 at an instance in time.

Figure 5A:
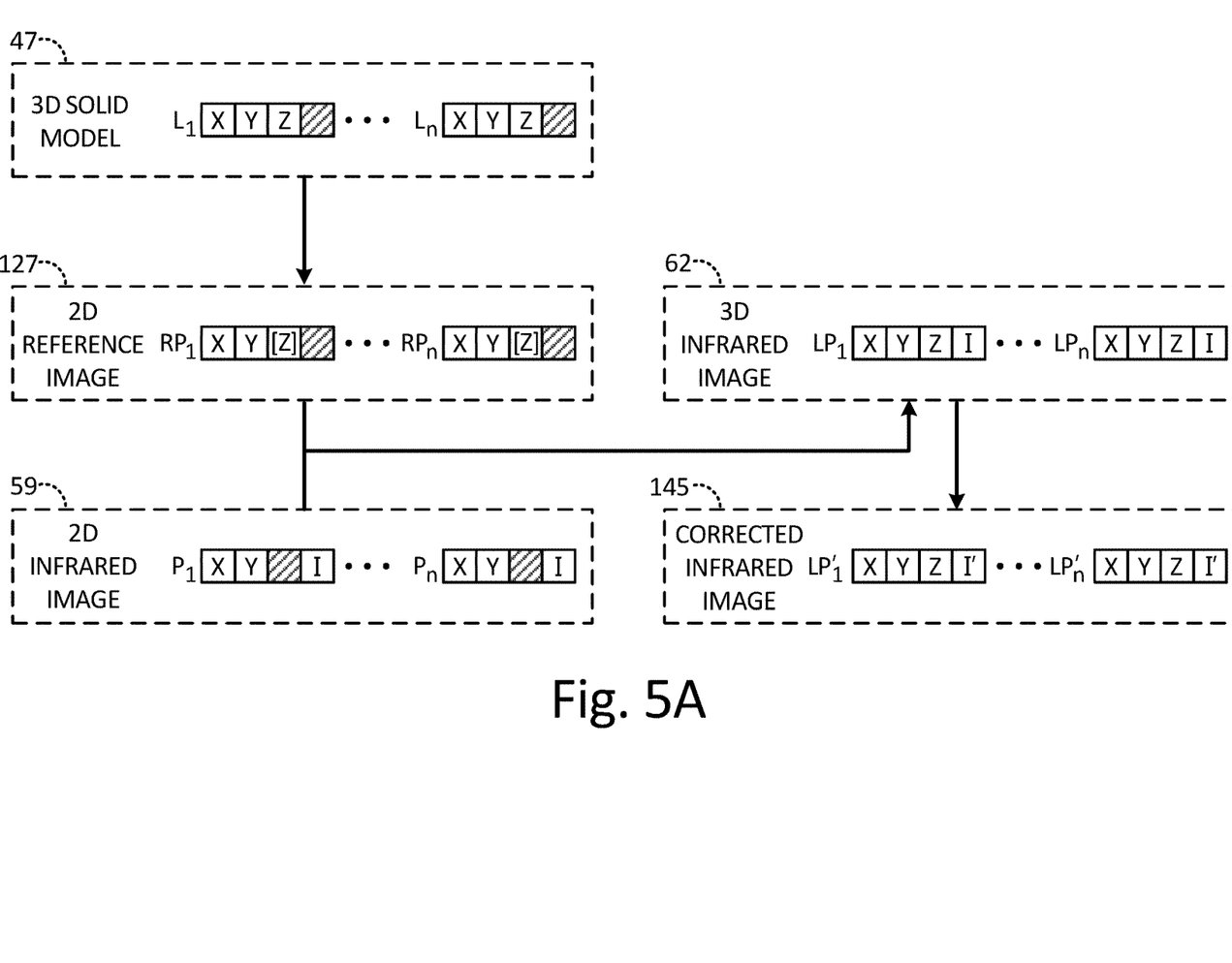
FIG. 5A is a schematic view of a mapping relationship between a two-dimensional infrared image and a three-dimensional solid model.

In one embodiment, a two-dimension to three-dimension mapping template can be used to correlate data (i.e., radiation heat transfer rate between component 14 and IR acquisition unit 10) associated with two-dimensional infrared image 59 to three-dimensional locations on component 14. The relationship between two-dimensional infrared image 59 and three-dimensional locations on component 14 is shown in FIG. 5A. Turning again to FIG. 4, generating a two-dimension to three-dimension mapping template (step 124) can include generating three-dimensional solid model 47 of component 14 (step 136), which can include a plurality of locations (L) (FIG. 5A). Each location (L) can have coordinates x, y, and z, corresponding to surface locations on component 14. Three-dimensional solid model 47 can be rendered or flattened to generate two-dimensional reference image 127 of component 14 (step 138). Two-dimensional reference image 127 can include a plurality of reference pixels (RP) (FIG. 5A). As shown in FIG. 5A, by rendering three-dimensional solid model 47 in this manner, each reference pixel ($RP_1 \ldots RP_n$) of two-dimensional reference image 127 can retain three-dimensional coordinates $((x,y,z)_1 \ldots (x,y,z)_n)$ of three-dimensional solid model 47, which correspond to surface locations on component 14. In other words, while two-dimensional reference image 127 is displayed using a flattened perspective projection of the component 14 retaining only camera-relative x and y coordinates, each pixel retains the true x, y, and z coordinates of three-dimensional solid model 47. Thus, reference pixels (RP) from two-dimensional reference image 127 can be correlated with actual three-dimensional locations on the surface of component 14. The value of n can be equal to the total number of pixels or three-dimensional coordinates.

Once generated, two-dimensional reference image 127 can be used to map two-dimensional infrared image 59 to three-dimensional locations on the surface of component 14. Mapping two-dimensional infrared image 59 to three-dimensional locations can be achieved by first mapping two-dimensional infrared image 59 to two-dimensional reference image 127. Two-dimensional infrared image 59 can be mapped to two-dimensional reference image 127 through an expert system such as a template matcher or neural network, which can use identifying features of component 14 (such as cooling holes 56 or component 14 form edges) to align two-dimensional infrared image 59 to two-dimensional reference image 127 of component 14 (step 126). As shown in FIG. 5A, a 1:1 relationship of infrared image pixels (P) to reference image pixels (RP) can allow for pixel by pixel mapping of pixels (P) of infrared image 59 to corresponding reference pixels (RP) of reference image 127, such that each reference image pixel (RP) can be associated with data (I) (e.g., radiation heat transfer rate) from the corresponding infrared image pixel (P).

To improve alignment accuracy between two-dimensional infrared image 59 and two-dimensional reference image 127, two-dimensional infrared image 59 can be divided into two-dimensional infrared sub-images 140 (shown as a single sub-image in FIG. 3) (step 141 of FIG. 4). Each sub-image 140 can include a plurality of pixels (P), but only a fraction of a total number of pixels (n) of the original two-dimensional infrared image 59. Each sub-image 140 can include a discrete and identifiable spatial region of component 14. In general, the size of sub-images 140 should not be so large that redundant identifying features (e.g., cooling holes 56, a trailing edge of airfoil 48, and platform 50, shown in FIG. 3) are included, and should not be so small that identifying features cannot be resolved (e.g., cannot distinguish a cooling hole 56 from a slot 58). The use of a template matcher or neural network to map two-dimensional infrared image 59 to two-dimensional reference image 127 can reduce the potential for errors that could otherwise result if either component 14 or IR acquisition unit 10 is shifted during imaging, such that a view angle or portion of component 14 being captured by IR acquisition unit 10 changes. Additionally, by utilizing template matching or a neural network, it is not necessary to place new components 14 in an exact location of a previously tested component 14. A new two-dimensional reference image can be obtained for each component 14 imaged by matching the orientation of three-dimensional solid model 47 with the orientation of component 14 relative to camera lens 16.

To reduce a computational load on processor 36, a subset of infrared sub-images 140 can be mapped to two-dimensional reference image 127. Generally, if only a subset of infrared sub-images 140 are to be mapped, sub-images 140 corresponding to regions of particular interest on component 14, such as a tip or cooling holes of a turbine blade, can be selected. In the disclosed embodiment, component 14 generally occupies 60-75 percent of two-dimensional infrared image 59 and roughly 40-80 percent of a component-occupying portion of infrared image 59 is mapped to two-dimensional reference image 127. However, this can be adjusted as appropriate according to the application or end use of component 14. For instance, components with multiple internal cooling channels extending through a large portion of component 14 may require mapping a greater portion of the infrared image to accurately predict cooling efficiency through distinct channels.

As shown in FIG. 5A, once two-dimensional infrared image 59 or portion of two-dimensional infrared image 59 is mapped to two-dimensional reference image 127, the pixels (P) of two-dimensional infrared image 59, containing the infrared data, can be mapped to the three-dimensional coordinates associated with each of the two-dimensional reference image pixels (RP) (step 128) to generate three-dimensional infrared image 62 and associated data (three-dimensional coordinates and radiation heat transfer rate). To reduce the computational load, a subset of the infrared image pixels (P) can be mapped to three-dimensional coordinates; however, generally a plurality of infrared image pixels (P) at least in a single infrared sub-image 140 are mapped to three-dimensional coordinates in effort to more accurately calculate surface temperatures over a given region of component 14.

Figure 5B:
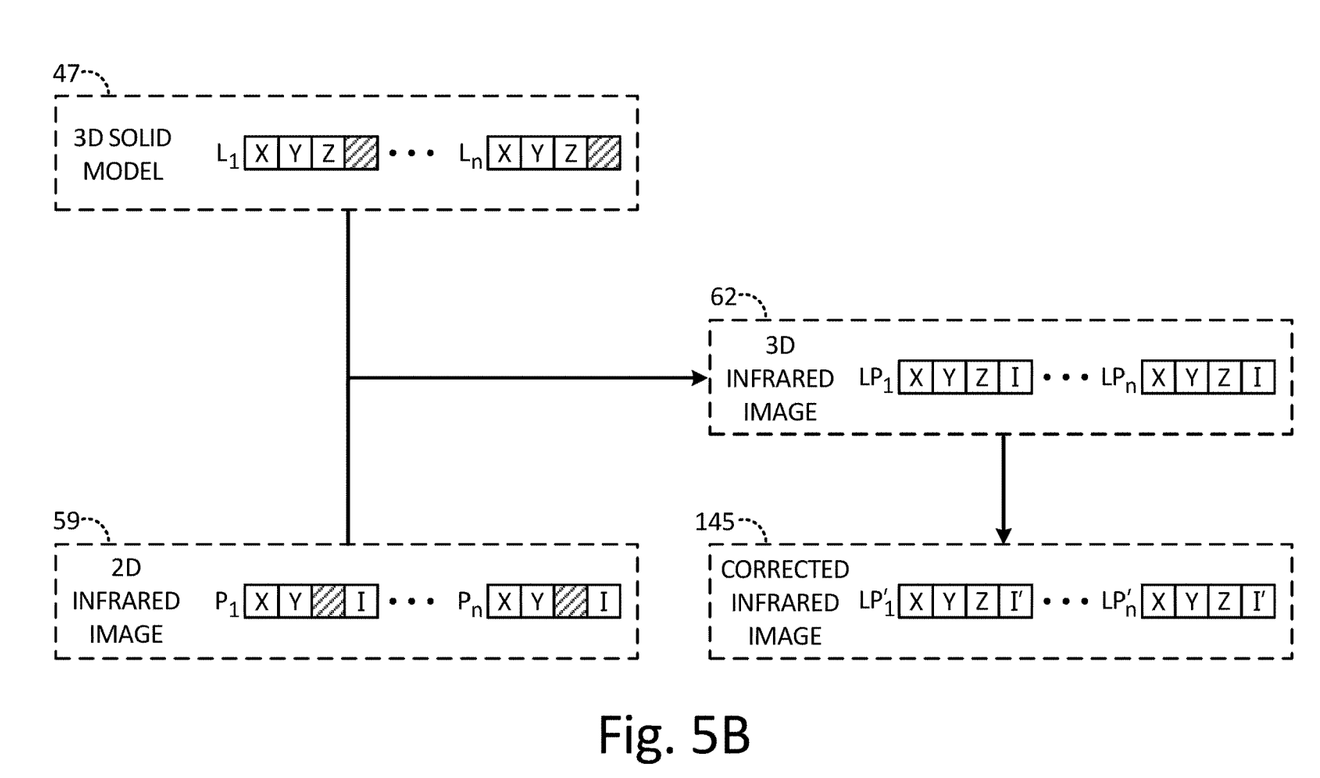
FIG. 5B is a schematic view of an alternative embodiment of a mapping relationship between a two-dimensional infrared image and a three-dimensional solid model.

In alternative embodiments, two-dimensional infrared image 59 can be translated directly to three-dimensional coordinates (indicated by line 142 in FIG. 4) using projection mapping or polynomial interpolation, each of which can provide a three-dimensional representation 62 of two-dimensional infrared image 59. When projection mapping and polynomial interpolation are used, steps 126 and 138 can be eliminated. FIG. 5B shows a schematic view of the mapping relationship between two-dimensional infrared image 59 and three-dimensional solid model 47 using either projection mapping or polynomial interpolation. In projection mapping, two-dimensional infrared image 59 can be projected onto three-dimensional solid model 47 of component 14. Because projection mapping does not use the two-dimensional template matching or neural network to match pixels (P) of infrared image 59 to corresponding pixels (RP) of reference image 127, projection mapping can be less accurate than pixel by pixel mapping. However, use of projection mapping can reduce the computational load and may be preferred for certain applications where a lower degree of accuracy can be tolerated. Polynomial interpolation can be particularly well suited for the inspection of components requiring a large view area where edges of the captured infrared image can be distorted or skewed. In polynomial interpolation, key reference points on two-dimensional infrared image 59 and on three-dimensional solid model 47 can be identified and a surface can be calculated using a polynomial fit (i.e., the infrared image can be shifted or skewed to fit an actual geometry of component 14). Although the present disclosure identifies template matching, neural networks, projection mapping, and polynomial interpolation as methods for translating two-dimensional infrared image 59 to three-dimensional coordinates correlating with surface locations on component 14, it will be understood by those skilled in the art that other image transform methods known in the art can be applied.

Once two-dimensional infrared image 59 and associated data has been mapped to the three-dimensional coordinates of component 14 using any of the foregoing methods, surface temperatures can be calculated for a plurality of locations along the surface of component 14 (step 130). Calculating surface temperatures over the three-dimensional representation of two-dimensional infrared image 59 requires calibrating a surface temperature calculation algorithm to correct for three-dimensional spatial variations along the surface of component 14 as well as other environmental factors (step 144) to generate corrected three-dimensional infrared image 145 (shown in FIG. 5A). Calibrations can first be made based on the first two-dimensional infrared image 59 captured. Because component 14 has been uniformly heated, it can be assumed that all locations on the surface of component 14 are at the same temperature at the time first two-dimensional infrared image 59 was captured. Therefore, any variations in incident pixel counts can be the result of spatial variations, variations in material emissivity, and external radiation sources. Corrections for spatial variations can be based on perspective angle calculated for a plurality of locations along the surface of component 14 based on a camera view angle of IR acquisition unit 10 in relation to each of the plurality of locations (step 146) on component 14 within the field of view. In the present disclosure, the perspective angle (shown in FIG. 1) is the angle α measured at a surface location between surface normal vector 12 of component 14 and vector 20, extending between the surface location and the focal location of lens 16. The corrections can be calculated as a shift in emissivity, which is a function of surface radiation heat transfer, based on the teachings of Dozier and Warren ("Effect of Viewing Angle on the Infrared Brightness Temperature of Snow," Water Resources Res., vol. 18, no. 5, p. 1424, October 1982). An updated emissivity can be used to calculate an initial infrared image temperature of component 14. Generally, spatial calibrations can be made once for the first two-dimensional image 59 captured and used for all subsequent infrared imaged 59 captured during inspection, calibrations can be adjusted throughout inspection, as needed, to correct for any movement of component 14 or IR acquisition unit 10.

In addition to correcting for three-dimensional spatial variations, environmental factors, such as humidity, impurities on the surface of component 14, and external radiation sources, which can affect the thermal image captured by IR acquisition unit 10, can be corrected for in the surface temperature calibration algorithm (step 144). Impurities as well as a constitution of the material of component 14 and heat treat cycles component 14 has gone through can change the emissivity of component 14, which can affect the thermal response captured by IR acquisition unit 10. Emissivity varies among different materials. Therefore, a smudge on component 14 can be identified on the infrared image because the material constituting the smudge has an emissivity different than that of the surrounding material. Emissivity corrections can generally be made using first two-dimensional infrared image 59, captured at an initial time at the start of inspection, but prior to active cooling. Because emissivity generally will not change during inspection, emissivity generally does not need to be reevaluated throughout inspection. In contrast, humidity can change during inspection and, therefore, multiple corrections to the calibration algorithm can be required throughout inspection based on a real-time measurement of humidity (step 148). Unless component 14 is isolated from external radiation sources (i.e., hot objects), mirror images of external radiation sources can be observed on the surface of component 14 in two-dimensional infrared image 59. Provided that thermal radiation of external radiation sources does not change during inspection, external radiation sources can be identified on first two-dimensional infrared image 59 and can be corrected for in the surface temperature calculations. Once surface temperature calculations have been calibrated to match the actual uniform or isothermal temperature of component 14, component 14 can be cooled and additional two-dimensional infrared images can be captured. New surface temperature for a plurality of surface locations over the time period of inspection can be calculated using the surface temperature calibrations made for the initial two-dimensional infrared image 59 captured as well as any additional corrections necessary to address changes in spatial or environmental factors (step 131).

The results generated from processing multiple two-dimensional images over a period of time during which surface temperatures of component 14 vary (time history of the temperature trace) can be used to estimate a maximum heat flux or rate of temperature change for a plurality of locations on component 14 (step 132). A qualitative performance indicator can be assigned to component 14 based on the maximum heat flux values (step 133). For components cooled by cooling fluid through internal channels, the qualitative performance indicator can be based on a maximum internal heat flux, calculated using calibrated surface temperatures, and a mass flow of cooling fluid. Calculating maximum heat flux values over large regions of the component can allow for a more accurate prediction of component performance during operation. In alternative embodiments, a qualitative performance indicator can be assigned to component 14 based on a single infrared image (indicated by arrow 150). Unlike spot check methods, which often include only single pixel references and limit component qualification to a simple pass/fail metric, evaluating a thermal response over a larger portion of component 14 allows for the evaluation of component 14 for use in a variety of applications. Instead of assigning component 14 a pass or fail based on limited information, component 14 can be designated for a particular end use including use in one or more environmental conditions within a range of environmental conditions. For example, component 14 can be assigned a performance indicator of moderate, as opposed to good or ideal, which may slot component 14 for use in lower performing engines or other applications. By more accurately evaluating thermal response of component 14, and thereby more accurately predicting operational performance in a respective environment, more components 14 can be qualified for use and fewer components 14 will be discarded.

The method used to map two-dimensional infrared images to three-dimensional coordinates of component 14 allows for the more accurate prediction of performance of component 14 within a representative environment of operational conditions. Although the disclosed method is particularly suited to turbine component qualification, it will be understood by those skilled in the art that the method can be applied to any three-dimensional component, structure, or workpiece, and is not limited to the application of gas turbine engines.

Discussion of Possible Embodiments

The following are non-exclusive descriptions of possible embodiments of the present invention.

A method for evaluating a turbine component includes inducing a thermal response of the component at an initial time, capturing a two-dimensional infrared image of the thermal response of the component with a thermal imaging device, wherein the two-dimensional infrared image comprises a plurality of infrared image pixels, generating a two-dimension to three-dimension mapping template to correlate two-dimensional infrared image data with three-dimensional locations on the component, mapping at least a subset of the plurality of infrared image pixels of the two-dimensional infrared image to three-dimensional coordinates using the mapping template, and generating a three-dimensional infrared image and infrared data of the component from the mapped infrared image pixels to three-dimensional coordinates, wherein the three-dimensional infrared image and infrared data is used to qualify the component for use.

The method of the preceding paragraph can optionally include, additionally and/or alternatively, any one or more of the following steps, features, configurations and/or additional components:

A further embodiment of the foregoing method further including capturing a second two-dimensional infrared image, wherein the first and second two-dimensional infrared images are separated by a time interval encompassing a transient thermal response induced by a change in thermal energy of the component.

A further embodiment of the foregoing method, wherein the step of capturing a two-dimensional infrared image can include capturing a rate of radiation heat transfer between the component and the thermal imaging device on each of the plurality of infrared image pixels.

A further embodiment of the foregoing method, the step of generating a two-dimension to three-dimension mapping template can include generating a three-dimensional solid model of the component, and generating a two-dimensional reference image of the component from the three-dimensional solid model. The two-dimensional reference image can include a plurality of reference pixels, each reference pixel can be associated with three-dimensional coordinates of the component as a function of three-dimensional coordinates of the three-dimensional solid model of the component.

A further embodiment of the foregoing method can further include the steps of dividing the two-dimensional infrared image into a plurality of infrared sub-images and mapping at least a subset of the plurality of infrared sub-images to corresponding spatial locations on the two-dimensional reference image of the component such that a plurality of infrared image pixels are mapped to a corresponding plurality of reference image pixels. Each infrared sub-image can include a discrete spatial region of the component and a portion of the plurality of infrared image pixels.

A further embodiment of the foregoing method, wherein the step of mapping the two-dimensional infrared image of the component to three-dimensional coordinates can include mapping at least a subset of the plurality of infrared image pixels to three-dimensional coordinates associated with the plurality of corresponding reference image pixels. Each of the plurality of infrared image pixels can include a rate of radiation heat transfer between the component and the thermal imaging device.

A further embodiment of the foregoing method, wherein the step of mapping the two-dimensional infrared image of the component to three-dimensional coordinates can include mapping each of the plurality of infrared image pixels in an infrared sub-image to three-dimensional coordinates associated with the plurality of corresponding reference image pixels.

A further embodiment of the foregoing method can further include the step of calculating a surface temperature for a plurality of locations along a surface of the component using the three-dimensional infrared image and data.

A further embodiment of the foregoing method, wherein the step of calculating a surface temperature can include calibrating the surface temperature calculation algorithm to correct for three-dimensional spatial variations in radiation heat transfer between the plurality of locations along the surface of the component and the thermal imaging device. Calibrating can include determining a view angle between a surface normal vector at each of the plurality of locations along the surface of the component and a vector between each of the plurality of locations and a focal location point of a lens of the thermal imaging device.

A further embodiment of the foregoing method, wherein the step of calculating a surface temperature can include calibrating a surface temperature calculation algorithm to correct for environmental factors selected from the group consisting of environmental humidity, material emissivity, external radiation sources, and combinations thereof.

A further embodiment of the foregoing method can further include the steps of changing the thermal response of the component over a period of time following the initial time, capturing a plurality of additional two-dimensional infrared images, and generating the three-dimensional infrared image and data for at least a subset of the plurality of additional two-dimensional infrared images. Each of the additional two-dimensional infrared images can be separated by a time interval within the period of time over which the thermal response changes, and each of the additional two-dimensional infrared images can capture a different thermal response than each of the other additional two-dimensional infrared images.

A further embodiment of the foregoing method can further include estimating a maximum internal heat flux for the component based on the three-dimensional infrared image and data for at least a subset of the plurality of additional two-dimensional infrared images.

A further embodiment of the foregoing method can further include flowing a cooling fluid through an internal channel of the component, determining a flow rate of the cooling fluid, and assigning a qualitative performance indicator to the component based on the maximum internal heat flux and a flow rate of the cooling fluid. The qualitative performance indicator can designate an end use of the component including one or more environmental conditions within a range of environmental conditions the component is qualified for use in.

A further embodiment of the foregoing method, wherein the step of mapping the two-dimensional infrared image of the component to three-dimensional coordinates can include using a technique selected from the group consisting of predetermined matched template correlating, projection mapping, and polynomial interpolation.

A further embodiment of the foregoing method can further include the steps of changing the thermal response of the component over a period of time following the initial time, capturing a plurality of additional two-dimensional infrared images, and generating the three-dimensional infrared image and data for at least a subset of the plurality of additional two-dimensional infrared images. Each of the additional two-dimensional infrared images can be separated by a time interval within the period of time over which the thermal response changes and each of the additional two-dimensional infrared images can capture a different thermal response than each of the other additional two-dimensional infrared images.

A method of evaluating a cooling efficiency of component for use in a gas turbine engine includes uniformly heating the component at an initial time such that surface temperatures are approximately equal at all surface locations on the component, capturing a two-dimensional infrared image of the component at the initial time with thermal imaging device, wherein the two-dimensional infrared image comprises a plurality of infrared image pixels, generating a two-dimension to three-dimension mapping template to correlate two-dimensional infrared image data with three-dimensional locations on the component, mapping at least a subset of the plurality of infrared image pixels of the two-dimensional infrared image to three-dimensional coordinates using the mapping template, and generating a three-dimensional infrared image and infrared data of the component from the mapped infrared image pixels to three-dimensional coordinates, wherein the three-dimensional infrared image and infrared data is used to qualify the component for use.

The method of the preceding paragraph can optionally include, additionally and/or alternatively, any one or more of the following steps, features, configurations and/or additional components:

A further embodiment of the foregoing method wherein the step of generating a two-dimension to three-dimension mapping template can include generating a three-dimensional solid model of the component, orienting the three-dimensional solid model of the component to match an orientation of the component with respect to a view angle of the thermal imaging device, and generating a two-dimensional reference image of the component from the three-dimensional solid model, wherein the two-dimensional reference image comprises a plurality of reference pixels. Each reference pixel can be associated with three-dimensional coordinates of the component.

A further embodiment of the foregoing method can further include dividing the two-dimensional infrared image into a plurality of infrared sub-images and mapping at least a subset of the plurality of infrared sub-images to corresponding spatial locations on the two-dimensional reference image of the component such that a plurality of infrared image pixels are mapped to a corresponding plurality of reference image pixels. Each infrared sub-image can include a discrete spatial region of the component and a portion of the plurality of infrared image pixels.

A further embodiment of the foregoing method can further include calculating a surface temperature for a plurality of locations along the surface of the component using the three-dimensional infrared image and data generated from the two-dimensional infrared image captured at the initial time, and calibrating the surface temperature calculation algorithm to correct for three-dimensional spatial variations along the surface of the component. Calibrating can include determining a view angle of the thermal imaging device in relation to each of the plurality of locations along the surface of the component.

A further embodiment of the foregoing method can further include flowing a cooling fluid through an internal channel of the component to change the thermal response of the component over a period of time following the initial time, capturing a plurality of additional two-dimensional infrared images, generating the three-dimensional infrared image and data for at least a subset of the plurality of additional two-dimensional infrared images, estimating a maximum internal heat flux for the component based on the three-dimensional infrared image and data for at least a subset of the plurality of additional two-dimensional infrared images, determining a flow rate of the cooling fluid, and assigning a qualitative performance indicator to the component based on the maximum internal heat flux and a flow rate of the cooling fluid. Each of the additional two-dimensional infrared images can be separated by a time interval within the period of time over which the thermal response changes and each of the additional two-dimensional infrared images can capture a different thermal response than each of the other additional two-dimensional infrared images. The qualitative performance indicator can designate an end use of the component including one or more environmental conditions within a range of environmental conditions the component is qualified for use in.

Summation

Any relative terms or terms of degree used herein, such as "substantially", "essentially", "generally", "approximately" and the like, should be interpreted in accordance with and subject to any applicable definitions or limits expressly stated herein. In all instances, any relative terms or terms of degree used herein should be interpreted to broadly encompass any relevant disclosed embodiments as well as such ranges or variations as would be understood by a person of ordinary skill in the art in view of the entirety of the present disclosure, such as to encompass ordinary manufacturing tolerance variations, incidental alignment variations, alignment or shape variations induced by thermal, rotational or vibrational operational conditions, and the like.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A method for evaluating a component for use in a gas turbine engine, the method comprising the steps of:
   inducing a thermal response of the component at an initial time;
   capturing a two-dimensional infrared image of the thermal response of the component with a thermal imaging device, wherein the two-dimensional infrared image comprises a plurality of infrared image pixels;
   generating a two-dimension to three-dimension mapping template to correlate two-dimensional infrared image data with three-dimensional locations on the component;
   mapping at least a subset of the plurality of infrared image pixels of the two-dimensional infrared image to three-dimensional coordinates using the mapping template;
   generating a three-dimensional infrared image and infrared data of the component from the mapped infrared image pixels to three-dimensional coordinates, wherein the three-dimensional infrared image and infrared data is used to qualify the component for use;
   wherein the step of generating a two-dimension to three-dimension mapping template comprises:
   generating a three-dimensional solid model of the component;
   generating a two-dimensional reference image of the component from the three-dimensional solid model, wherein the two-dimensional reference image comprises a plurality of reference pixels, each reference pixel being associated with three-dimensional coordinates of the component as a function of three-dimensional coordinates of the three-dimensional solid model of the component;
   dividing the two-dimensional infrared image into a plurality of infrared sub-images, each infrared sub-image comprising a discrete spatial region of the component and a portion of the plurality of infrared image pixels; and
   mapping at least a subset of the plurality of infrared sub-images to corresponding spatial locations on the two-dimensional reference image of the component such that a plurality of infrared image pixels are mapped to a corresponding plurality of reference image pixels.

2. The method of claim 1, wherein the step of capturing a two-dimensional infrared image comprises capturing a rate of radiation heat transfer between the component and the thermal imaging device on each of the plurality of infrared image pixels.

3. The method of claim 1, wherein the step of mapping the two-dimensional infrared image of the component to three-dimensional coordinates comprises mapping at least a subset of the plurality of infrared image pixels to three-dimensional coordinates associated with the plurality of corresponding reference image pixels, wherein each of the plurality of infrared image pixels comprises a rate of radiation heat transfer between the component and the thermal imaging device.

4. The method of claim 3, wherein the step of mapping the two-dimensional infrared image of the component to three-dimensional coordinates comprises:
   mapping each of the plurality of infrared image pixels in an infrared sub-image to three-dimensional coordinates associated with the plurality of corresponding reference image pixels.

5. The method of claim 3, further comprising the step of:
calculating a surface temperature for a plurality of locations along a surface of the component using the three-dimensional infrared image and data.

6. The method of claim 5, wherein the step of calculating a surface temperature comprises:
calibrating the surface temperature calculation algorithm to correct for three-dimensional spatial variations in radiation heat transfer between the plurality of locations along the surface of the component and the thermal imaging device, wherein calibrating comprises determining a view angle of the thermal imaging device for each of the plurality of locations along the surface of the component.

7. The method of claim 6, wherein the step of calculating a surface temperature comprises:
calibrating a surface temperature calculation algorithm to correct for environmental factors selected from the group consisting of environmental humidity, material emissivity, external radiation sources, and combinations thereof.

8. The method of claim 7 further comprising the steps of:
changing the thermal response of the component over a period of time following the initial time;
capturing a plurality of additional two-dimensional infrared images, wherein each of the additional two-dimensional infrared images are separated by a time interval within the period of time over which the thermal response changes, and wherein each of the additional two-dimensional infrared images captures a different thermal response than each of the other additional two-dimensional infrared images; and
generating the three-dimensional infrared image and data for at least a subset of the plurality of additional two-dimensional infrared images.

9. The method of claim 8, wherein calibrating a surface temperature calculation algorithm is done using the three-dimensional infrared image and data for at least one of the additional two-dimensional infrared images.

10. The method of claim 9, further comprising the step of:
flowing a cooling fluid through an internal channel of the component;
determining a flow rate of the cooling fluid; and
assigning a qualitative performance indicator to the component based on the maximum internal heat flux and a flow rate of the cooling fluid, wherein the qualitative performance indicator designates an end use of the component including one or more environmental conditions within a range of environmental conditions the component is qualified for use in.

11. The method of claim 8, further comprising the step of:
estimating a maximum internal heat flux for the component based on the three-dimensional infrared image and data for at least a subset of the plurality of additional two-dimensional infrared images.

12. The method of claim 1, wherein the step of mapping the two-dimensional infrared image of the component to three-dimensional coordinates comprises using a technique selected from the group consisting of predetermined matched template correlating, projection mapping, and polynomial interpolation.

13. The method of claim 12, further comprising the steps of:
changing the thermal response of the component over a period of time following the initial time;
capturing a plurality of additional two-dimensional infrared images, wherein each of the additional two-dimensional infrared images are separated by a time interval within the period of time over which the thermal response changes, and wherein each of the additional two-dimensional infrared images captures a different thermal response than each of the other additional two-dimensional infrared images; and
generating the three-dimensional infrared image and data for at least a subset of the plurality of additional two-dimensional infrared images.

14. A method of evaluating a component for use in a gas turbine engine, the method comprising:
uniformly heating the component at an initial time such that surface temperatures are approximately equal at all surface locations on the component;
capturing a two-dimensional infrared image of the component at the initial time with a thermal imaging device, wherein the two-dimensional infrared image comprises a plurality of infrared image pixels;
generating a two-dimension to three-dimension mapping template to correlate two-dimensional infrared image data with three-dimensional locations on the component;
mapping at least a subset of the plurality of infrared image pixels of the two-dimensional infrared image to three-dimensional coordinates using the mapping template;
generating a three-dimensional infrared image and infrared data of the component from the mapped infrared image pixels to three-dimensional coordinates, wherein the three-dimensional infrared image and infrared data is used to qualify the component for use;
wherein the step of generating a two-dimension to three-dimension mapping template comprises:
generating a three-dimensional solid model of the component;
orienting the three-dimensional solid model of the component to match an orientation of the component with respect to a view angle of the thermal imaging device;
generating a two-dimensional reference image of the component from the three-dimensional solid model, wherein the two-dimensional reference image comprises a plurality of reference pixels, each reference pixel being associated with three-dimensional coordinates of the component;
dividing the two-dimensional infrared image into a plurality of infrared sub-images, each infrared sub-image comprising a discrete spatial region of the component and a portion of the plurality of infrared image pixels; and
mapping at least a subset of the plurality of infrared sub-images to corresponding spatial locations on the two-dimensional reference image of the component such that a plurality of infrared image pixels are mapped to a corresponding plurality of reference image pixels.

15. the method of claim 14, further comprising the step of:
calculating a surface temperature for a plurality of locations along the surface of the component using the three-dimensional infrared image and data generated from the two-dimensional infrared image captured at the initial time; and
calibrating the surface temperature calculation algorithm to correct for three-dimensional spatial variations along the surface of the component, wherein calibrating comprises determining the view angle of the thermal imaging device in relation to each of the plurality of locations.

16. The method of claim 15, further comprising the steps of:

flowing a cooling fluid through an internal channel of the component to change the thermal response of the component over a period of time following the initial time;

capturing a plurality of additional two-dimensional infrared images, wherein each of the additional two-dimensional infrared images are separated by a time interval within the period of time over which the thermal response changes, and wherein each of the additional two-dimensional infrared images captures a different thermal response than each of the other additional two-dimensional infrared images;

generating the three-dimensional infrared image and data for at least a subset of the plurality of additional two-dimensional infrared images;

estimating a maximum internal heat flux for the component based on the three-dimensional infrared image and data for at least a subset of the plurality of additional two-dimensional infrared images;

determining a flow rate of the cooling fluid; and assigning a qualitative performance indicator to the component based on the maximum internal heat flux and a flow rate of the cooling fluid, wherein the qualitative performance indicator designates an end use of the component including one or more environmental conditions within a range of environmental conditions the component is qualified for use in.

\* \* \* \* \*